United States Patent [19]
Suttie
[11] 4,021,568
[45] May 3, 1977

[54] RODENTICIDAL COMPOSITIONS CONTAINING 2-CHLORO-3-PHYTYL-1,4-NAPHTHAQUINONE AND WARFARIN

[75] Inventor: John W. Suttie, Madison, Wis.

[73] Assignee: Wisconsin Alumni Research Foundation, Madison, Wis.

[22] Filed: May 12, 1975

[21] Appl. No.: 576,347

Related U.S. Application Data

[63] Continuation-in-part of Ser. No. 359,632, May 14, 1973, abandoned.

[52] U.S. Cl. .................................. 424/281; 424/331
[51] Int. Cl.[2] ....................... A01N 9/24; A01N 9/28
[58] Field of Search ............... 424/17, 84, 281, 331

[56] References Cited

UNITED STATES PATENTS 2,687,365 8/1954 Link .................................... 424/17
3,113,071 12/1963 Derse et al. ......................... 424/17

OTHER PUBLICATIONS

Lowenthal et al., Can. J. Chem., 48, pp. 3957–3958 (1970).
Lowenthal et al., Chem. Abst. vol. 67 (1967) 89407s.
Lowenthal et al., Chem. Abst. vol. 55 (1961) p. 5767.

*Primary Examiner*—Allen J. Robinson
*Attorney, Agent, or Firm*—Howard W. Bremer

[57] ABSTRACT

A rodenticide suitable for the control of rat populations containing anticoagulant rodenticide-resistant rats comprising as the active rodenticidal ingredients 2-chloro-3-phytyl-1,4-naphthaquinone and a 3-substituted-4-hydroxycoumarin anticoagulant or a 2-substituted 1,3 indandione.

2 Claims, No Drawings

RODENTICIDAL COMPOSITIONS CONTAINING 2-CHLORO-3-PHYTYL-1,4-NAPHTHAQUINONE AND WARFARIN

The invention described herein was made in the course of work under a grant or award from the Department of Health, Education, and Welfare. This application is a continuation-in-part of application Ser. No. 359,632, filed May 14, 1973, now abandoned.

This invention relates to rodenticides and food baits containing them.

More specifically, this invention relates to anticoagulant-type rodenticides.

Certain indandione derivatives and 3-substituted 4-hydroxycoumarin anticoagulant rodenticides, particularly warfarin, because of their efficacy and safety, have, for many years, been the rodenticides of choice over the quick-acting stomach poisons. it is recognized that these anticoagulant rodenticides function by suppressing the synthesis of the vitamin K-dependent clotting factors in the rodent and causing internal hemorrhaging. Such rodenticides are multiple dose baits, i.e., they normally have to be eaten over a period of about 3–6 days in order to be effective.

Some years ago strains of wild rats which were resistant to the action of anticoagulant rodenticides, as represented specifically by warfarin, were discovered in a number of areas in Scotland, Wales, and northern Europe. More recently, this trait has been found in rats in certain areas of the United States (see W. B. Jackson et al, Science, 176, 1343 (1972) and the resistance reported is to a number of different coumarin and indandione derivatives (see C. M. Boyle, Nature, 188, 517 (1960); J. H. Freaves et al, J. Hyg (Lond.), 67, 311 (1969); and D. C. Drummond et al, E.P.P.O. Intern. Conference (Paris), pp. 57–59 (1967)).

It has now been found that these strains of anticoagulant-resistant rats can be effectively controlled through the use of 2-chloro-3-phytyl-1,4-naphthaquinone as the active rodenticide. This compound, which for purposes here will be referred to as chloro-K, in contrast to the 3-substituted 4-hydroxycoumarin anticoagulants, appears to function as a direct antagonist of vitamin K.

It is reported that the warfarin anticoagulant rodenticide-resistant trait is an inherited one (see Greaves et al, Nature, 215, 877(1967) and Nature, 224, 284 (1969) and not related to alterations in warfarin metabolism (Greaves et al, Nature, 215 supra and Hermodson et al, Am. J. Physiol., 217, 1316 (1969). It has also been shown that rats which are resistant to the warfarin induced anticoagulant action have a greatly increased requirement for vitamin K (Hermodson et al, supra) but that the metabolism of that vitamin is unaffected (M. J. Thierry et al, Am. J. Physiol., 219, 854 (1970)). This indicates that higher tissue concentrations of both the vitamin and the anticoagulant are needed for biological activity, and suggests that the mutation might well be one which has influenced a binding site on a protein that is a receptor both for vitamin K and the anticoagulant. It was fully expected therefore that a compound with a modified vitamin K structure, such as chloro-K, would bind to the genetically altered protein receptor site less readily than it would to a normal receptor site. Consequently, it was totally unexpected that the chloro-K would exhibit more effective anticoagulant rodenticidal activity in anticoagulant rodenticide-resistant rats than it does in normal rats.

In the following Examples the chloro-K used was prepared from 2-chloro-1,4-naphthaquinone in accordance with the procedure of Lowenthal et al, Can. J. Chem., 48, 3957 (1970).

EXAMPLE 1

The efficacy of the chloro-K as a blood anticoagulant was shown by injecting an aqueous solution containing 2 mg of chloro-K, 14 mg of Tween-80 (a surface-active emulsifying agent consisting of oleate esters of polyoxyethylene sorbitan marketed by Armour & Co. of Chicago, Ill.) and 10 mg. of ethanol per ml. into the tail vein of the rats 21 hours before blood was drawn by cardiac puncture and analyzed for prothrombin. (The analysis was by the two stage method of Ware and Seegers as modified by Shapiro & Waugh, Thromb, Diath, Haemorrhag., 16, 496, (1966)).

The anticoagulant rodenticide-resistant rats used were descendants of a colony homozygous for the trait. These rats were fed a normal commercially available laboratory chow, e.g. Purina Rat Chow, marketed by Ralston Purina Co. of St. Louis, Mo., or Wayne Lab-Blox, marketed by Allied Mills Inc. of Chicago, Ill., and, except when on experiments, were given water ad libitum containing 0.5 mg/l of menadione sodium bisulfate (trihydrate) to maintain normal prothrombin concentration. (Normal plasma prothrombin levels are 220–250 units/ml.) Prothrombin concentrations in these rats are not affected by an intraperitoneal injection of 5 mg. of warfarin per kg of body weight or by feeding them a diet containing 0.025% warfarin.

Results obtained are shown in the following table.

Table 1

Effect of the Chloro Analog of Vitamin $K_1$ on Prothrombin Synthesis

| Dose of Chloro-K | Normal Rats | | Warfarin-Resistant Rats | |
|---|---|---|---|---|
| | Male | Female | Male | Female |
| 0.2 mg/kg | — | 240±8* | — | 113±19 |
| 0.4 | — | 230±5 | — | 88±10 |
| 2.0 | 204±12 | 189±26 | 27±6 | 72±10 |
| 4.0 | — | 166±9 | — | 68±10 |

Units of prothrombin per ml of plasma ± S.E.

It can be seen from the above table that chloro-K is an effective blood anticoagulant in warfarin-resistant rats; is considerably more effective for that purpose in this strain than in normal rats; and is a more effective anticoagulant in male warfarin-resistant rats (male warfarin-resistant rats have a higher vitamin-K requirement than females)- all of which suggested that chloro-K might have potential as a rodenticide in geographical areas where rat populations can no longer be controlled by the commonly used anticoagulants.

Since under normal field conditions, anticoagulant rodenticide-resistant rats are interspersed with so-called normal rats (rats which do not exhibit resistance to anticoagulant rodenticides), a rodenticide to be generally effective under such conditions would comprise ingredients to which both kinds of rats would be susceptible. In accordance with the teachings of the present invention, the ingredient of choice effective against the rats in a given population which are characterized by a resistance to anticoagulant rodenticides would be chloro-K. An ingredient effective against the so-called normal rats would, of choice, be one of the commonly used anticoagulant rodenticides. Among these the 3-substituted 4-hydroxycoumarins are the most popular with warfarin the leader among these. It is well recognized that the requisite for anticoagulant activity among the coumarin compounds is that they be characterized by being 4-hydroxycoumarins which are substituted only at the 3-position (no substituent in the benzene ring). Also, the substituent in the 3-position must be a substituted benzyl group or its equivalent. Examples of such compounds having such substituent benzyl group are: warfarin, 3-($\alpha$-acetonylbenzyl)-4-hydroxycoumarin, and its water-soluble sodium salt; phenprocoumon, 3-($\alpha$-ethylbenzyl)-4-hydroxycoumarin) and its chloro derivatives, 3($\alpha$-ethyl-p-chlorobenzyl-4-hydroxycoumarin; and Coumachlor, 3-($\alpha$-acetonyl-4-chlorobenzyl-4-hydroxycoumarin. An example of an effective anticoagulant rodenticide having an equivalent of the substituted benzyl group in the 3-position is Fumarin, 3-($\alpha$-acetonyl furfuryl)-4-hydroxycoumarin. Other well-known anticoagulant rodenticides which can be effectively used in the rodenticides of this invention are the indandione compounds Pival, 2-pivalyl-1,3,indandione and Diphacinone, 2-diphenylacetyl-1,3 indandione. The equivalency for rodenticidal purposes of Pival, Diphacinone, warfarin and Coumachlor are shown by Hayes et al in Public Health Reports, Vol. 74, No. 2, February 1959.

For purposes of the present invention combinations of chloro-K with one or more of the anticoagulant rodenticides selected from the group consisting of the 3-substituted-4-hydroxycoumarin anticoagulants, Pival and Diphacinone are suitable. More specifically, in the rodenticides of this invention the combination of chloro-K with one or more of the anticoagulant rodenticides selected from the group consisting of warfarin, phenprocoumon, Coumachlor, Fumarin, Pival and Diphacinone are eminently satisfactory. These anticoagulants can be used in combination with the chloro-K in concentrations which are well recognized in the art. These concentrations range from about 0.0005% to about 0.2% by weight of the food bait in which they are incorporated (see for example U.S. Letters Patent No. 3,113,071).

EXAMPLE 2

The rodenticidal efficacy of diets containing varying amounts of warfarin or chloro-K alone or in admixture were conducted on normal and warfarin-resistant rats (see description in Example 1).

The diet used was the standard Environmental Protection Agency rodenticide test diet consisting of 65% coarse ground corn, 25% ground oats, 5% powdered sugar and 5% corn oil. The chloro-K, warfarin, and chloro-K and warfarin mixtures were dissolved in corn oil and the then toxified corn oil was added to the diet in amount 5% by weight of the diet. These diets containing the anticoagulants were the only food available to the rats during each 20 day test period.

The results obtained are shown in the following table wherein the closed circles represent male rats and the open circles female rats. The normal rats are designated (N) and warfarin-resistant rats (WR). The percentage of warfarin (WARF) and chloro-K (cl-K) fed in the diets is indicated in the bottom line.

Table 2

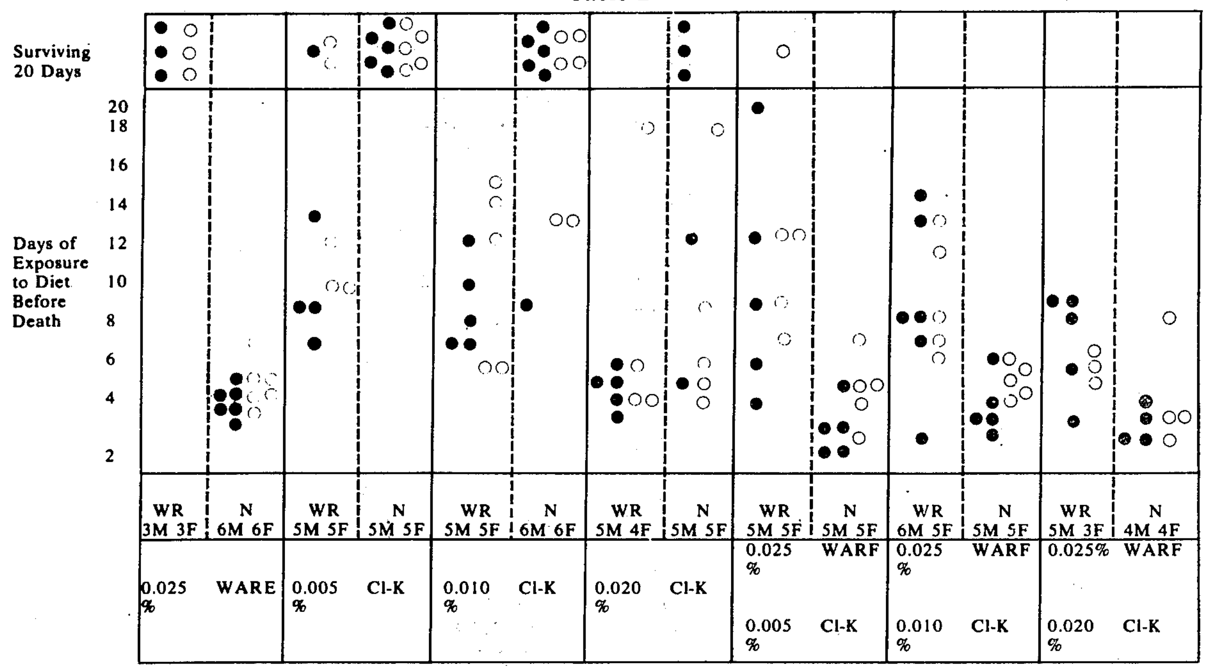

EXAMPLE 3

The procedures described in Example 2 were followed in evaluating, at the concentrations shown in the table below, the efficacy of chloro-K, pival (2-pivalyl-1,3-indandione) and chloro-K-pival mixtures in the control of normal and anticoagulant-resistant rats (the rats were from the same colony described in Example 1 above).

The results obtained are shown in Table 3 wherein the legends applied are the same as in Table 2 above.

Table -continued

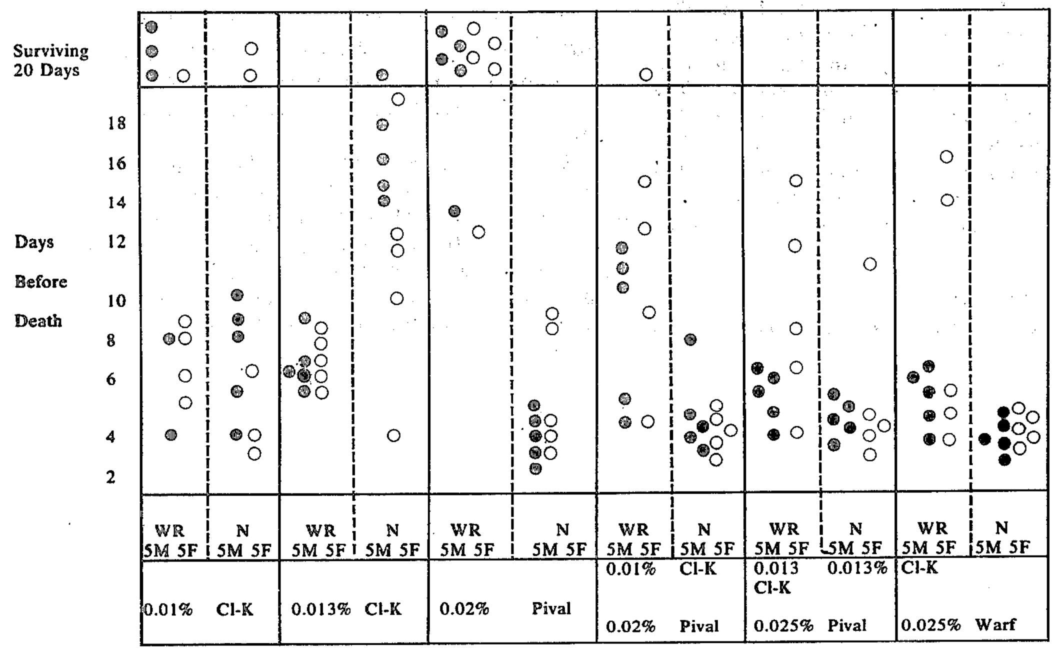

It is apparent from the foregoing that chloro-K in amounts of about 0.02% shows significant rodenticidal efficacy even against normal rats and that against anticoagulant-resistant rats it has a significant rodenticidal effect in concentrations as low as 0.005% by weight of the rodenticide bait. Amounts in excess of 0.02% by weight are, of course, usable, the maximum amount being dictated only by economic considerations. Amounts of chloro-K in the range from about 0.005% to about 0.03% have been found to be quite suitable. Little real benefit is gained insofar as rodenticidal efficacy is concerned, however, above about 0.025%.

For purposes of the present invention the preferred rodenticide food bait contains about 0.025% by weight of an anticoagulant rodenticide and about 0.02% by weight of chloro-K in combination. With this combination, both strains of rat, i.e., the anticoagulant rodenticide-resistant rat and the normal rat, are killed in about one week.

It is also apparent that in any given locale where only anticoagulant rodenticide-resistant rats are encountered, chloro-K can be used as the sole rodenticide in a rodenticide food bait. In addition, chloro-K alone or in combinaion with other anticoagulant rodenticides can be used to control other rodent pest populations such as mice as shown in the following Example.

EXAMPLE 4

Wild mice (Mus musculus) were trapped from local infestations. These mice were divided into two groups. One group (24 mice) was maintained on the diet shown in Example 2 to which had been added 5% by weight of corn oil containing 0.025% warfarin by weight of the diet. The second group (28 mice) was maintained on the diet shown in Example 2 to which had been added 5% by weight of corn oil containing 0.025% chloro-K by weight of the diet. Results are shown in the table below.

Table 4

| Rodenticide in Diet | Number Dead 7 days | Number Dead 17 days |
|---|---|---|
| Warfarin | 16 | 24 |
| Chloro-K | 15 | 25 |

It is evident from the above data that chloro-K is effective to control mice populations.

EXAMPLE 5

The rodenticidal efficacy of a diet containing in admixture chloro-K and Fumarin (3-(α-acetonyl furfuryl)-4-hydroxycoumarin) as the active rodenticidal ingredients was determined on normal and warfarin-resistant rats. The chloro-K and Fumarin were present, respectively, in amounts 0.02% by weight and 0.025% by weight of the diet. The diet was that described in Example 2 and the method of addition of the rodenticidal agents was accomplished as shown in that Example.

The results obtained are set forth in the table below wherein the data given represents all of the rats in the test. The closed circles represent male rats, the open circles female rats, N represents normal rats and WR the warfarin-resistant rats.

Table 5

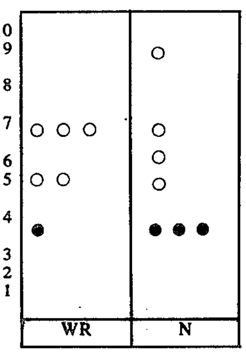

The food used in the bait of the present invention can be any edible product such as, for example, cracked corn, corn meal, mixtures of various grains, e.g. mixtures of corn, oats and wheat, ground meat, and mixtures of meat and grain, etc. For purposes of safety, however, it is preferred to use a grain base which, while attractive to the rodent, is not as attractive to children and household pets as a bait containing meat or like edible products. The final bait mixtures can be used as such or be pelleted in accordance with standard practices in the art.

What is claimed is:

1. A rodenticide suitable against rat populations including anticoagulant rodenticide-resistant rats, said rodenticide containing, as the essential rodenticidal ingredients, 2-chloro-3-phytyl-1,4-naphthaquinone in an amount about 0.02% by weight and warfarin or its water soluble sodium salt in an amount about 0.025% by weight.

2. A rodenticide food bait suitable against rat populations including anticoagulant rodenticide-resistant rats which comprises edible material acceptable to rats and, as the essential rodenticidal ingredients, 2-chloro-3-phytyl-1,4-naphthaquinone in an amount about 0.02% by weight and warfarin or its water soluble sodium salt in an amount about 0.025% by weight.

* * * * *

UNITED STATES PATENT OFFICE
CERTIFICATE OF CORRECTION

Patent No. 4,021,568 Dated May 3, 1977

Inventor(s) John W. Suttie

It is certified that error appears in the above-identified patent and that said Letters Patent are hereby corrected as shown below:

Column 6, lines 55 to 65, Table 5,

"

| | WR | N |
|---|---|---|
| 10 | | |
| 9 | | o |
| 8 | | |
| 7 | ooo | o |
| 6 | | o |
| 5 | oo | o |
| 4 | ● | ●●● |
| 3 | | |
| 2 | | |
| 1 | | |

" should be "

| | WR | N |
|---|---|---|
| 10 | | |
| 9 | | o |
| 8 | | |
| 7 | oo● | o |
| 6 | | ● |
| 5 | ●o | o |
| 4 | ● | ●●● |
| 3 | | |
| 2 | | |
| 1 | | |

".

Signed and Sealed this

*nineteenth* Day of *July 1977*

[SEAL]

*Attest:*

RUTH C. MASON
*Attesting Officer*

C. MARSHALL DANN
*Commissioner of Patents and Trademarks*